US000001078H

United States Statutory Invention Registration [19]

[11] Reg. Number: H1078

Norris et al. [43] Published: Jul. 7, 1992

[54] SYNTHESIS OF 5,7-DIAMINO-4,6-DINITROBENZOFUROXAN

[75] Inventors: William P. Norris; David J. Vanderah; Michael P. Kramer, all of Ridgecrest, Calif.

[73] Assignee: The United States of America as represented by the Secretary of the Navy, Washington, D.C.

[21] Appl. No.: 519,625

[22] Filed: May 7, 1990

[51] Int. Cl.[5] ..... C07D 271/12; C07D 285/14

[52] U.S. Cl. ..... 548/126

[58] Field of Search ..... 548/126

[56] References Cited

U.S. PATENT DOCUMENTS 4,754,040 6/1988 Chafin ..... 548/126

OTHER PUBLICATIONS

Potts, Comprehensive Heterocyclic Chemistry v.6 pp. 411-112 (1984).

March, Advanced Organic Chemistry p. 600 (1985).

*Primary Examiner*—Richard D. Lovering

*Assistant Examiner*—Joseph D. Anthony

*Attorney, Agent, or Firm*—Melvin J. Sliwka; Stuart H. Nissim; Donald E. Lincoln

[57] ABSTRACT

5,7-Diamino-4,6-dinitrobenzofuroxan is synthesized in high yield by amination of 7-amino-4,6-dinitrobenzofuroxan with hydroxylamine in the presence of strong base such as potassium hydroxide. Acidification of the potassium salt produces a fine powder. Recrystallization of the powder by an extraction process under vacuum in solvents such as dimethylformamide results in large, cube-like crystals which can be pressed to high density explosive formulations. These explosive formulations show high performance as explosives.

8 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SYNTHESIS OF 5,7-DIAMINO-4,6-DINITROBENZOFUROXAN

TECHNICAL FIELD

The present invention relates to the synthesis of an insensitive, thermally stable, high-density, high-performance explosive and, more particularly, this invention relates to an improved synthesis of 5,7-Diamino-4,6-dinitrobenzofuroxan (CL-14) in high yield from readily available, insensitive starting materials.

BACKGROUND OF THE INVENTION 5,7-Diamino-4,6-dinitrobenzofuroxan (CL-14) has a positive heat of formation and high density which leads to a better than predicted detonation velocity. The explosive properties of CL-14, trinitrotoluene (TNT) and RDX are compared in Table 1.

TABLE 1

COMPARISON OF EXPLOSIVE PROPERTIES

| Explosive | CL-14 | TNT | RDX |
|---|---|---|---|
| Impact sensitivity, cm | 129 | 50 | 19 |
| Detonation velocity (calculated) mm/μs | 8.05 | 6.67 | 8.95 |
| Detonation velocity (measured) mm/μs | 8.22 | 6.96 | 8.85 |

CL-14 is much less sensitive to impact than either TNT or RDX, is much more powerful than TNT and approaches RDX in power (detonation velocity).

DESCRIPTION OF THE PRIOR ART

CL-14 has been synthesized by two different syntheses. In the first synthesis disclosed in U.S. patent application Ser. No. 259,203, the dinitrobenzofuroxan precursor is aminated in 2 stages to form CL-14 in 45% yield. The yield is too low and the synthesis is dangerous since the dinitro precursor is a sensitive explosive having higher sensitivity than RDX.

In the second synthesis, 5,7-dichloro-4,6-dinitrobenzofuroxan was prepared in four steps starting with o-nitroaniline. CL-14 is obtained by reacting the dichloro precursor with ammonia followed by acidification. CL-14 was obtained in high overall yield of 62%. However, the synthesis contained too many steps to be industrially useful.

STATEMENT OF THE INVENTION

In the synthesis of the invention CL-14 is provided in higher yield from readily available, insensitive starting materials in a minimum number of steps. Recrystallization by an extraction technique provides large cube-like crystals. These crystals when formulated as a molding powder can be pressed to more than 97% of maximum theoretical density. Detonation studies show that CL-14 performs about as predicted by calculations when compared to RDX.

CL-14 is prepared in the synthesis of the invention by amination of 7-amino-4,6-dinitrobenzofuroxan (ADNBF) with hydroxylamine in the presence of strong base to form a salt from which CL-14 is recovered by acidification with a strong acid. The intermediate salt is prepared in a yield of over 69% and the CL-14 is recovered in a yield of over 65%.

ADNBF is available in large quantity commercially or can readily be prepared in high yield in a two step synthesis starting with a common material, m-nitroaniline. ADNBF is a much safer starting material. ADNBF is an insensitive explosive like TNT whereas 4,6-dinitrobenzofuroxan, a previously used starting material, is more sensitive than RDX.

Better control of particle size of the recovered CL-14 is provided by the invention, larger uniformly-sized crystals result from recrystallization by an extraction technique. The larger crystals can be pressed in formulations to near maximum theoretical density, i.e. 97.3%. Pressed pellets of CL-14 detonated in a plate dent test demonstrated a performance level of 91.4% compared to cyclotrimethylenetrinitramine (RDX). The small failure diameter makes the large crystal CL-14 useful in many ordnance applications.

These and many other features and attendant advantages of the invention will become clear as the description proceeds.

DETAILED DESCRIPTION OF THE INVENTION

The amination of ADNBF is conducted by hydroxylamine in at least a stoichiometric amount of hydroxylamine in the presence of strong base at a temperature favoring optimum amination. Hydroxylamine is usually used in the form of a salt of a strong acid such as hydrochloric acid or sulfuric acid. The strong base is usually a Group I metal hydroxide such as sodium or potassium hydroxide in a concentration usually from 1N to 5N. Potassium hydroxide is preferred since the low solubility of the potassium salt of CL-14 facilitates higher recovery of the precipitated material. Isolation and recovery of the sodium salt is much more difficult. Amination by hydroxylamine is optimum at temperatures below about 20° C. Temperatures at which the reaction mixture freezes are avoided.

CL-14 is recovered as a precipitate by acidification of the salt of CL-14 with a strong acid. Representative strong acids are sulfuric acid, hydrochloric acid or phosphoric acid usually in a concentration from 0.5N to 10N. The CL-14 precipitates in the form of submicrometer sized particles making it necessary to recrystallize the particles to a larger size. Formulation and pressing of this fine powder gives only about 85% of the theoretical maximum density (TMD).

Recrystallization by the usual technique—solution at high temperature followed by slow cooling—still results in fine crystals. However, extraction at the proper temperature with a suitable solvent results in large crystals having a particle size above 1 micrometer. Representative organic solvents for extraction of CL-14 are acetonitrile, dimethylformamide, acetone, nitromethane or N-methylpyrrolidinone. Dimethylformamide, acetone and N-methylpyrrolidinone all gave cube-like crystals. The largest crystals resulted from the use of reagent grade dimethylformamide.

The synthesis of CL-14 using ADNBF and KOH is shown in the following reaction scheme:

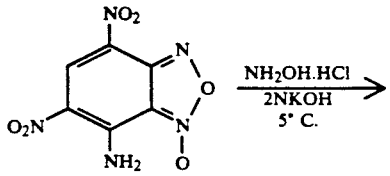

ADNBF

-continued

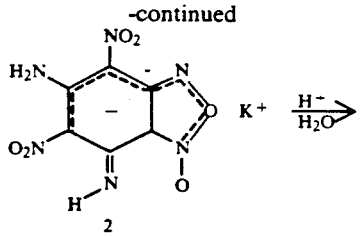

2

69.4% yield
CL-14 Salt

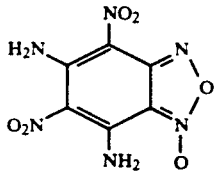

CL-14
94% yield
65.2% overall yield

The invention is illustrated by the following detailed examples of synthesis of CL-14.

ADNBF can be purchased commercially or can be synthesized as described by Hobin et al. (1) or according to the following procedure.

Preparation of ADNBF

With stirring, 4.87 g (0.0738 mol) of $NaN_3$ (99%) were added all at once to 10.00 g (0.0366 mol) of 2,3,4,6-tetranitroaniline suspended in 100 mL glacial acetic acid at 25° C. The reaction vessel was immersed in a 25° C. water bath. Gas evolution was vigorous and the temperature in the reaction vessel rose to 40° C. in 4 minutes. The temperature dropped to 30° C. after another 6 minutes and gas evolution has slowed considerably. Yellow solid was suspended in the reaction solvent. The reaction mixture was then heated, and at about 67° C., the suspended solids all dissolved to give a light-orange-colored solution. Heating was continued and at 80° C. (about 4 minutes later) solids began separating. Gas evolution was moderate. After 1 hour at 80° C., gas evolution was ceased. The reaction mixture was allowed to stand at 25° C. for 6 hours. Solids were filtered from the reaction mixture, washed with 200 mL $H_2O$ (25° C.) on filter funnel, dried, and weighed to give 8.48 g (96.1% yield) of ADNBF.

Analysis calculated for $C_6H_3N_5O_6$: C, 29.89; H, 1.25; N, 29.05. Found: C, 29.66; H, 1.28; N, 28.60. Elemental analysis of the product agrees quite well with theoretical values, although N is a little low.

Preparation of 5,7-Diamino-4,6-dinitrobenzofuroxan (CL-14) From 7-amino-4,6-dinitrobenzofuroxan (ADNBF)

Hydroxylamine hydrochloride, 4.16 g (0.0602 mol), was added to a stirred solution of 40.0 g (0.606 eq) of 85% KOH made up to 300 mL with $H_2O$ at a temperature of 5° C. To this mixture, 5.33 g (0.0221 mol) of 7-amino-4,6-dinitrobenzofuroxan was added, with stirring at 5° C. Initially, a transient bright-red color appeared then changed to an orange color. Solid particles were visible in the stirred reaction mixture at all times. Stirring was continued at 5° C. for 5 hr. The reaction mixture was poured into 500 mL of ice water and stirred for 15 min. The fine yellow solid was filtered off, washed with two-50 mL portions of ice water (on the filter), and dried to give 4.51 g (69.4% yield) of the potassium salt of CL-14, (measured density of $1.976 \pm 0.008$ g/cm$^3$ and an impact sensitivity ($H_{50}$) of 59 cm (2.5 kg wt)).

The potassium salt was stirred with 50 mL of 3N HCl for 30 min, the yellow solid was filtered off, washed with 50 mL of $H_2O$ on the filter, and dried to give 3.69 g (65.2% yield) of CL-14. The decomposition temperature and the infrared spectrum of this product are comparable to those reported for CL-14 in U.S. patent application Ser. No. 259,203.

As previously discussed, conventional recrystallization results in fine crystals. In studies of CL-14 it was found that the pressed and cast-cured formulations prepared from the small CL-14 crystals had very low percentages of theoretical maximum density (TMD) and disappointingly low solids loading. The problem was attributed to the small particle size.

The extractive recrystallization technique of the invention provides larger sized crystals resulting in high performance explosive formulations.

The recrystallization is conducted using an extractor divided into two chambers by a fritted glass separator and a vapor by-pass between the two chambers. A reflux condenser is attached to the upper chamber. A vacuum pump is used to regulate the pressure of the system as needed. Solvent is placed in the bottom chamber and the CL-14 powder is placed on the fritted glass separator disc. The solvent is heated to reflux while stirring with a large magnetic stirring bar. Stirring prevents bumping as the CL-14 precipitates. The temperature is usually from about 50° C. to about 130° C. as adjusted by the system pressure. The reflux rate is adjusted such that the upper chamber above the glass frit separator is maintained about two-thirds full of liquids and solids.

The CL-14 is extracted through the fritted disc to the lower chamber. Gradually CL-14 concentration increases in the bottom flask and crystallizes from the boiling extraction solvent. The extraction is continued until complete, usually at about 50 hours. The contents of the bottom flask are then filtered while still hot and then washed with solvent and dried.

Recrystalization of CL-14 From Dimethylformamide (DMF)

Ninety grams of CL-14 powder were placed above a fritted glass disc of the extractor along with 200 mL of DMF. 1000 mL of DMF was added to a 2-L, round-bottomed flask, which was attached to the bottom of the extractor. A condenser was placed at the top of the extractor and the pressure in the system was reduced to 155 mm of mercury. The contents of the 2-L flask were heated to reflux while stirring with a large magnetic stirring bar. The temperature in the 2-L pot was 103° C. The reflux rate was controlled to keep the chamber above the glass frit about two-thirds full of liquid and solids. After 48 hr, extraction was complete and the contents of the 2-L flask were filtered while still hot. The solids on the filter were washed with two-50-mL portions of fresh DMF, then with two-50-mL portions of acetone, and dried to give 62 g of sparkling yellow solid. Analysis on a Malvern Instruments Easy Particle Sizer M3.0 gave the average particle size as 50.4 μm. Examination under a microscope showed the particles to be cube-like in shape.

Upon cooling and standing for several days, the dark filtrate precipitated an additional 20 g of rather fine CL-14 particles, which could be filtered off and recycled for use in the next extractive recrystallization.

For extractions with other solvents, a similar procedure was followed. Because of the much lower solubility of CL-14 in acetone, nitromethane, and acetonitrile, a longer period of extraction time was required. Results are presented in Table 2.

TABLE 2

CL-14 RECRYSTALLIZATION BY EXTRACTION

| Solvent | Temperature/ pressure | Average particle size, $\mu$[a] | Particle shape[b] |
|---|---|---|---|
| Acetonitrile | 79° C./atm | 24.9 | needles ~6:1 |
| Dimethylformamide[c] | 103° C./155 mm | 50.4 | cube-like |
| Acetone | 55° C./atm | 10.7 | cube-like |
| Nitromethane | 99° C./atm | 11.5 | needles |
| N-Methyl-pyrrolidinone | 107° C./32 mm | 26.8 | cube-like[d] |

[a]Malvern Instruments Easy Particle Sizer, M3.0.
[b]Optical microscope.
[c]Reagent grade used directly from the bottle.
[d]A small amount of rubbery polymeric material separated with the CL-14.

As shown in Table 2, dimethylformamide, acetone, and N-methylpyrrolidinone give cube-like crystals, which are desirable for pressing and casting formulations. Acetonitrile and nitromethane give needles that give lower percentages of maximum theoretical densities when used in pressings or castings and are, therefore, not desirable. Dimethylformamide gives the larger average size particle. N-Methylpyrrolidinone deposited a small amount of rubbery polymer with the recrystallized CL-14, thus making the N-methylpyrrolidinone undesirable for use. Formulation and pressing were performed with CL-14 recrystallized from dimethylformamide by the extraction process.

Preparation of the CL-14/EVA Molding Powder Formulation

A lacquer was prepared from 15 mL of ethyl acetate and 1.8 g of ethylene/vinyl acetate. After the mixture was heated and stirred until all of the EVA was dissolved, 18.2 g of recrystallized CL-14 (50 $\mu$m average particle size) was added to the mixture. The mixture was stirred by hand, using a Teflon spatula, until most of the ethyl acetate solvent had evaporated. With alternate stirring and heating in a 60° C. oven, the solvent was largely removed to leave a fine powder. The powder was placed in a 60° C. oven for 16 hr in preparation for pressing.

Pressing of CL-14 Molding Powder

A 20-ton press was calibrated to 40,000 psi for a ½-inch die set. The die set is fitted with a jacket for heating and is also fitted with a connection to allow evacuation of the die cavity during the pressing operation. The preheated CL-14 molding powder was added to the heated die set. Temperatures of both the molding powder and the die set were approximately 60° C. After the die piston was in place, the die chamber was evacuated to 5 mm pressure. Pressing was then completed by raising the die pressure to 40,000 psi and then holding that pressure for 5 min. The pressure and vacuum were released and the finished pellet of explosive was extracted from the die. The length and diameter of the pellet were carefully measured and the percentage of theoretical maximum density of the weighed pellet was calculated.

The pressing conditions were chosen to optimize the TMDs of the formulations. All of the pressings gave ½-inch-diameter by 1-inch-long pellets. Two pellets of each formulation were pressed and the percent TMDs reported are the average of the two pellets. In addition the pressings of CL-14 were compared to pressing of PBXC-13 (RDX/EVA) and PBXC-17 (HMX/EVA). Results follow:

TABLE 3

CL-14 PRESSING STUDIES

| Pressed | Composition by weight | % TMD |
|---|---|---|
| CL-14 | CL-14/EVA[a] (91/9) | 97.3 |
| PBXC-13 | RDX/EVA (91/9)[b] | 95.7 |
| PBXC-17 | HMX/EVA (91/9) | 98.3 |

[a]Ethylene-vinyl acetate copolymer.
[b]Holston Production Plant material, as received.

The molding powder of recrystallized CL-14 is comparable in density to PBXC-13, a qualified RDX-based explosive and only slightly below PBXC-17, a HMX based explosive.

Using the plate dent test, the depths of dents made in a witness plate by selected explosives can be compared against the depth of a dent made by a known explosive with a known detonation pressure. For this test series, a combination of 95% HMX and 5% Viton A (PBXN-5) was chosen as the standard and all explosive formulations, including the standard, were pressed under the same conditions: vacuum, 40,000 psi, 5 minute dwell time, 60° C. The results are summarized in Table 4.

TABLE 4

COMPARATIVE PLATE DENT RESULTS

| Explosive | Plate dent, inches | % of standard |
|---|---|---|
| PBXN-5 (standard)[a] | 0.126 | 100.0 |
| CL-14/EVA[b] | 0.085 | 67.5 |
| PBXC-13 | 0.093 | 73.8 |
| PBXC-17 | 0.095 | 75.4 |
| PBXW-7[c] | 0.081 | 64.3 |

[a]The dents have all been normalized to 100% TMD.
[b]This formulation is the same as in Table 3.
[c]TATB formulation.

The plate dent test was conducted using two 1-inch-long by ½-inch-diameter cylinders stacked on a 1-inch-thick witness plate. A ½-inch by ½-inch cylinder or PBXN-5 (to act as booster) and a RP-80 detonator (to initiate the explosive train) were placed on top of each stack. All of the PBXN-5 booster pellets were pressed to within ±0.20% density of each other.

The detonated pressed CL-14 pellets demonstrate a performance level of 91.4% compared to RDX. On the basis of this test the failure diameter is less than ½ inch, which makes CL-14 useful in many ordnance applications. CL-14 exhibits a measured detonation velocity of 8.22 mm/$\mu$s, a calculated detonation pressure of 295K bar and an Impact Sensitivity ($H^{50}$) of 129 cm. TNT has an Impact Sensitivity of 50 cm.

A new, more efficient synthesis route for synthesizing CL-14, starting with ADNBF, is provided. CL-14 can be successfully recrystallized using the extraction technique of the invention to give cube-like crystals of an average size of 50 $\mu$m, which can be formulated and pressed to pellets with 97.3% TMD. The results of the plate dent test show that CL-14 performs at 91.4% of the level of RDX, which approximates the calculated performance level. Furthermore, since the diameter of the cylinder tested is ½ inch, the failure diameter of CL-14 is less than ½ inch. This small failure diameter will make CL-14 useful for both small booster and large main charge applications.

Cited Reference

1. T. P. Hobin. "Some Aminodinitro Derivatives of Benzofurazan and Benzofurazanoxide", Tetrahedron, Vol. 24 (1968), pp. 6145–6148.

It is to be realized that only preferred embodiments of the invention have been described and that numerous substitutions, modifications and alternations are permissible without departing from the spirit and scope of the invention as defined in the following claims.

What I claim is:

1. A method of synthesizing 5,7-Diamino-4,6-dinitrobenzofuroxan comprising the steps of:

aminating 7-amino-4,6-dinitrobenzofuroxan with a salt of hydroxylamine in the presence of a strong base to form a salt; and acidifying the salt to recover 5,7-Diamino-4,6-dinitrobenzofuroxan.

2. A method according to claim 1 in which the strong base is a Group I metal hydroxide in a concentration from 0.5N to 5N.

3. A method according to claim 2 in which the strong base is potassium hydroxide.

4. A method according to claim 2 in which the hydroxylamine is a salt of a strong acid.

5. A method according to claim 1 in which the amination is conducted at a temperature below 20° C.

6. A method according to claim 2 in which the salt is acidified with a strong acid to precipitate 5,7-Diamino-4,6-dinitrobenzofuroxan as a fine powder.

7. A method according to claim 6 in which the concentration of the strong acid is from 0.5N to 10N.

8. A method according to claim 7 in which the strong acid is selected from the group consisting of sulfuric acid, hydrochloric acid and phosphoric acid.

* * * * *